(12) United States Patent
Yao et al.

(10) Patent No.: US 6,673,973 B1
(45) Date of Patent: Jan. 6, 2004

(54) METHOD OF PRODUCING 1,1-BIS-(4-HYDROXYPHENYL)-3,3,5-TRIMETHYLCYCLOHEXANE

(75) Inventors: Kazuhiko Yao, Wakayama (JP); Kenji Ekawa, Wakayama (JP); Yoichiro Isota, Wakayama (JP); Toru Nakaguchi, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/363,207

(22) PCT Filed: Sep. 11, 2000

(86) PCT No.: PCT/JP00/06205

§ 371 (c)(1),
(2), (4) Date: Mar. 6, 2003

(87) PCT Pub. No.: WO02/22534

PCT Pub. Date: Mar. 21, 2002

(51) Int. Cl.$^7$ .............................................. C07C 39/17
(52) U.S. Cl. ..................................................... 568/721
(58) Field of Search .......................................... 568/721

(56) References Cited

U.S. PATENT DOCUMENTS

| | | | |
|---|---|---|---|
| 5,227,458 A | * | 7/1993 | Freitag |
| 5,336,812 A | * | 8/1994 | Salek |
| 5,783,733 A | * | 7/1998 | Kissinger |
| 6,284,931 B1 | * | 9/2001 | Isota |

FOREIGN PATENT DOCUMENTS

JP  2000-159711  *  6/2000

* cited by examiner

*Primary Examiner*—Michael L. Shippen
(74) *Attorney, Agent, or Firm*—Merchant & Gould P.C.

(57) ABSTRACT

A process for production of 1,1-bis(4-hydroxyphenyl)-3,3,5-trimethylcyclohexane which comprises reacting phenol with 3,3,5-trimethylcyclohexanone in the presence of an acid catalyst, adding an aqueous solution of an alkali to the resulting reaction mixture to neutralize it, removing a water phase from the thus neutralized reaction mixture, cooling the resulting oil phase to crystallize phenol adduct crystals of 1,1-bis(4-hydroxyphenyl)-3,3,5-trimethylcyclohexane while obtaining a primary crystallization filtrate, wherein the primary crystallization filtrate is heated to a temperature of 150–250° C. in the presence of an alkali catalyst in an inert gas atmosphere under a reduced pressure to thermally decompose 1,1-bis(4-hydroxyphenyl)-3,3,5-trimethylcyclohexane in the primary crystallization filtrate.

1 Claim, No Drawings

METHOD OF PRODUCING 1,1-BIS-(4-HYDROXYPHENYL)-3,3,5-TRIMETHYLCYCLOHEXANE

TECHNICAL FIELD

The invention relates to a process for production of 1,1-bis(4-hydroxyphenyl)-3,3,5-trimethylcyclohexane (referred to as "BPTMC" hereinafter). More particularly, the invention relates to a process for production of BPTMC by an acid condensation reaction of phenol with 3,3,5-trimethylcyclohexanone (referred to as "TMC" hereinafter) wherein the filtrate which is obtained in the crystallization and filtration step for the resulting reaction product is heated as it is thereby not only to reduce the amount of residue (industrial wastes) generated in the reaction which cannot be recovered for reuse but also to recover phenol efficiently.

BACKGROUND ART

In recent years, BPTMC is used as raw materials for the production of optical products such as optical disks, as well as synthetic resins for optical use such as polycarbonate resins for optical use. In order to supply BPTMC to this use, it is demanded to produce uncolored high purity BPTMC which is free of by-products, and besides free of high boiling point by-products or colored by-products derived from purification processes for the obtained reaction product and residual phenol or trace impurities such as sodium in high selectivity and in high yield in an industrially stable manner.

A variety of processes for the production of BPTMC are already known. According to one of such processes, phenol is reacted with TMC using hydrogen chloride gas as a catalyst and an alkyl mercaptan as a promoter in the presence of an inactive organic solvent or in the absence of a solvent and then phenol remained unreacted is removed from the reaction mixture by steam distillation, as described in Japanese Patent Application Laid-open No. 2-88634. It is also described therein that, after the reaction, water is added to the reaction mixture, and then an alkali to neutralize the reaction mixture, followed by heating, cooling and removing an aqueous phase, thereby obtaining the desired BPTMC.

A further process is known, as is described in Japanese Patent Application Laid-open No. 8-505644. According to the process, phenol is reacted with TMC using hydrogen chloride gas as a catalyst and an alkyl mercaptan such as octanethiol as a promoter. After the reaction, water is added to the reaction mixture to form a slurry, and the slurry is filtered to provide 1:1 adduct crystals of BPTMC and phenol, and then the phenol is removed from the adduct crystals, thereby providing the desired BPTMC.

A process is also known, as described in Japanese Patent Application Laid-open No. 4-282334. The process provides the desired BPTMC by the reaction of phenol with TMC using water-insoluble cation exchange resins having sulfonic acid groups therein as a catalyst and a mercaptan compound as a promoter. In Japanese Patent Application Laid-open No. 5-213803, there is described a process in which an acid catalyst such as benzenesulfonic acid is added to a mixture of phenol, TMC, a mercaptan compound as a promoter and water, whereupon the reaction is started with stirring, and the desired BPTMC is obtained in high selectivity.

However, according to the known processes, phenol is used usually in a large excess relative to TMC so that it is important how to recover unreacted phenol efficiently and how to recycle to the reaction. In particular, the filtrate which is obtained by crystallizing and collecting the desired reaction product after the completion of the reaction contains phenol, BPTMC dissolved in the phenol, and reaction by-products such as isomers, it is very important to treat the filtrate efficiently to recover phenol in an economical manner, but also to reduce the amount of the resulting residue (industrial wastes) as much as possible in order to produce BPTMC advantageously in an industrial scale.

On the other hand, in respect of 2,2-bis(4-hydroxyphenyl)propane (referred to as "bisphenol A" hereunder), a process for production including reuse of filtrate from a crystallization stage after the completion of the reaction is proposed. For example, Japanese Patent Application Laid-open No. 5-345737 describes a process as follows. Phenol adduct crystals of bisphenol A are crystallized out of a phenol solution containing bisphenol A, the crystals are collected by filtration, the resulting mother liquor is subjected to distillation to recover the phenol and the thus recovered phenol is recycled to the reaction stage. The bottom liquid in a distilling tower is heated and decomposed in the presence of an alkali catalyst. The resulting substance is recovered under a reduced pressure and purified by using an ion exchange resin, followed by recycling to the reaction.

In Japanese Patent Application Laid-open No. 6-321834, it is described that after phenol adduct crystals of bisphenol are crystallized and separated out of the reaction mixture, the resulting mother liquor is made contact with an acid catalyst to isomerize o- and p-isomers to p- and p'-isomers, and then the resulting isomers are recycled back to the crystallization stage for reuse.

Further in Japanese Patent Application Laid-open No. 10-59888, the following is described. Phenol is reacted with acetone in the presence of an ion exchange resin catalyst to produce bisphenol A, and the bisphenol A produced is led to a phenol removal unit to separate unreacted phenol therefrom. The obtained bisphenol A is led to a melt crystallizer to separate residual phenol and isomers therefrom. The separated phenol and isomers are cracked, and the thus recovered phenol is recycled back to the reaction stage for reuse.

However, it is difficult to predict the behavior of formation of BPTMC by a condensation reaction of TMC which is an alicyclic ketone having three methyl groups in the molecule with phenol based on the behavior of production of bisphenol A by a condensation reaction of acetone and phenol. As a matter of fact, nothing has been known how to treat a filtrate efficiently which is obtained from the steps of crystallizing and filtering the reaction products and contains phenol and BPTMC dissolved in the phenol and how to treat the resulting filtrate to reduce the amount of the resulting residue (industrial wastes) as much as possible while how to recover the phenol efficiently so that BPTMC can be produced advantageously in an industrial manner.

The invention has been accomplished to solve such problems as involved in the known processes for the production of BPTMC by an acid condensation reaction of phenol and TMC.

Therefore, it is an object of the invention to provide a process for production of BPTMC advantageously in an industrial manner in which phenol adduct crystals of BPTMC are crystallized and separated from the reaction mixture and the resulting filtrate is treated effectively to reduce the amount of residue (industrial wastes) which can not be recovered for reuse, but also to recover phenol efficiently so that BPTMC is produced advantageously in an industrial manner.

SUMMARY OF THE INVENTION

The invention provides a process for production of 1,1-bis(4-hydroxyphenyl)-3,3,5-trimethylcyclohexane which comprises reacting phenol with 3,3,5-trimethylcyclohexanone in the presence of an acid catalyst, adding an aqueous solution of alkali to the resulting reaction mixture to neutralize it, removing a water phase from the thus neutralized reaction mixture, cooling the resulting oil phase to crystallize phenol adduct crystals of 1,1-bis(4-hydroxyphenyl)-3,3,5-trimethylcyclohexane while obtaining a primary filtrate, wherein the primary filtrate is heated to a temperature. of 150–250° C. in the presence of an alkali catalyst in an inert gas atmosphere under a reduced pressure to thermally decompose the 1,1-bis(4-hydroxyphenyl)-3,3, 5-trimethylcyclohexane contained in the primary filtrate.

BEST MODE FOR CARRYING OUT THE INVENTION

According to the invention, phenol is reacted with TMC in the presence of an acid catalyst (reaction step), an alkali solution is added to the resulting reaction mixture to neutralize it (neutralization step), the resulting phenol adduct crystals of BPTMC are dissolved in the thus neutralized reaction mixture, a water phase is removed from the reaction mixture, the resulting oil phase is cooled to crystallize the phenol adduct crystals out of the oil phase and the phenol adduct crystals are collected by filtration while a primary filtrate is obtained (primary crystallization and filtration step).

If necessary, the adduct crystals are added to a crystallization solvent composed of an aromatic hydrocarbon such as toluene and water, the mixture is heated to dissolve the adduct crystals therein, a water phase is removed and the resulting oil phase is cooled to crystallize BPTMC out of the oil phase, and the crystals are collected by filtration (secondary crystallization and filtration step), thereby providing high purity crystals of BPTMC while a secondary crystallization filtrate is obtained.

Furthermore, if necessary, after removing water, a part of the primary crystallization filtrate may be recycled to the reaction step.

When an aromatic hydrocarbon such as toluene or water is added to the oil phase in the primary crystallization step, the resulting primary crystallization filtrate may be heated as it is, or the filtrate may be heated according to the invention after removing such a crystallization solvent or water by suitable means. However, it is preferred that no such crystallization solvent is used when the primary crystallization is carried out.

The primary crystallization filtrate obtained in the primary crystallization and filtration step is usually composed of 80–90% by weight of organic components comprised of unreacted phenol, BPTMC dissolved in the phenol and others (by-products such as isomers and polymeric material) and 10–20% by weight of water. The organic components are composed of, for example, 80–90% by weight of phenol, 3–7% by weight of BPTMC and 5–10% by weight of the others.

According to the invention, the primary crystallization filtrate obtained in the primary crystallization and filtration step, preferably containing no crystallization solvent, is treated. Namely, an alkali catalyst is added to the primary crystallization filtrate and is then heated. However, if necessary, at least a part of the primary crystallization filtrate is recycled as it is in the reaction step and at least a part of the rest may be treated according to the invention.

More specifically, an alkali catalyst is added to the primary crystallization filtrate and is heated so that BPTMC dissolved in the phenol in the filtrate is thermally decomposed. The alkali catalyst usable includes, for example, alkaline metal hydroxides such as sodium hydroxide or potassium hydroxide. The alkaline metal hydroxide is used usually in an amount of 0.002–0.2% by weight, preferably in an amount of 0.004–0.05% by weight, based on the weight of the primary crystallization filtrate. The alkali is used usually in the form of aqueous solution, preferably having a concentration of 10–48% by weight.

According to the invention, the primary crystallization filtrate is heated in an atmosphere of an inert gas such as nitrogen, helium or argon under a reduced pressure of 2–4Kpa until the temperature of the filtrate finally reaches 150–250° C., preferably 160–220° C. In this manner, phenol in the primary crystallization filtrate is recovered. Moreover, as a result of thermal decomposition of BPTMC, phenol and decomposition by-products are formed.

Accordingly, the residue generated by heating the primary crystallization filtrate in this manner contains substantially no BPTMC having a high melting point so that the residue is liquid of low viscosity at a temperature less than 100° C. and is easily handled. Consequently, the amount of residue that cannot be recovered for reuse can be reduced. On the other hand, the phenol generated in this heating treatment can also be recovered together with the phenol in the primary crystallization filtrate and reused.

The primary crystallization filtrate may be heated from the first to a temperature of 150–250° C. in the presence of an alkali catalyst, or the primary crystallization filtrate may be first heated to a temperature at which water, the crystallization solvent that may be present in the filtrate or phenol is distilled off, and after these are distilled off, the filtrate may be heated so that it finally reaches a temperature of 150–250° C.

When the primary crystallization filtrate is heated at a temperature less than 150° C. in the presence of an alkali catalyst, BPTMC in the filtrate is only insufficiently thermally decomposed, whereas when the primary crystallization filtrate is heated at a temperature more than 250° C., by-products are generated in the filtrate and the amount of residue after the heat treatment of the primary filtrate increases. In addition, the productivity of the production of the desired product decreases on account of energy loss.

Industrial Applicability

As described above, an alkali catalyst is added to the primary crystallization filtrate as it is, and the filtrate is simply heated in an inert atmosphere under a reduced pressure. By this single heat treatment operation according to the invention, phenol in the filtrate is recovered, but also BPTMC dissolved in the phenol in the filtrate is decomposed to phenol and low molecular weight decomposition by-products, thereby remarkably reducing the amount of residue (industrial wastes) that cannot be recovered for reuse after the treatment of the filtrate. This process is in contrast to a process wherein the primary crystallization filtrate is treated in many steps, for example, distilled, thermally decomposed, and distilled under a reduced pressure for recovery of phenol and BPTMC.

Furthermore, the resulting residue generated in the process of the invention has a low viscosity and easily handled. On the other hand, the phenol generated by the thermal decomposition of BPTMC is recovered together with the phenol in the primary crystallization filtrate, and can be reused as it is.

EXAMPLES

The invention is described in more detail with reference to examples, but the invention is not limited these examples.

Reference Example 1

112.8 g (1.2 mol) of phenol, 16.9 g of water, 0.5 g of 75% aqueous solution of phosphoric acid and 7.2 g of crystals of BPTMC were placed in a one liter capacity four-necked flask provided with a thermometer, a dropping funnel, a reflux condenser and a stirrer to prepare a slurry containing phenol adduct crystals of BPTMC.

The slurry was adjusted at a temperature of 20° C. After the inside the flask was replaced by nitrogen gas, hydrogen chloride gas was introduced into the flask under stirring. 4.2 g of 15% aqueous solution of sodium methyl mercaptide was added dropwise to the slurry while the slurry was maintained at a temperature of 20° C., and then a mixture of 112.8 g (1.2 mol) of phenol and 42.0 g (0.3 mol) of TMC was added dropwise to the slurry over a period of six hours. The reaction mixture was found to increase in temperature during the addition, and when the addition was completed, the temperature was found to be 40° C. Then, the reaction was further continued at a temperature of 40° C. for anther three hours under stirring.

After the reaction, 18% aqueous solution of sodium hydroxide was added to the reaction mixture so that it was neutralized to have a pH of 6.5 while it was maintained at a temperature of 40–50° C. The thus neutralized reaction mixture was heated to a temperature of 95° C. so that the phenol adduct crystals of BPTMC produced were dissolved therein.

Water was removed from the reaction mixture, and the resulting oily substance was cooled to a temperature of 30° C. to crystallize phenol adduct crystals of BPTMC. The adduct crystals were collected by filtration while a filtrate (primary crystallization filtrate) was obtained.

Example 1

1000 g of the primary crystallization filtrate which was obtained in the Reference Example 1 and contained 16.3 g of water, 707.0 g of phenol, 47.0 g of BPTMC and 83.0 g of others (such as isomers and by-products) were placed together with 1.0 g of 48% aqueous solution of sodium hydroxide in a one liter capacity four-necked flask provided with a thermometer, a distillation tube, a reflux condenser and a stirrer in a nitrogen atmosphere. The mixture was heat-treated at a temperature of 160° C. for two hours under a reduced pressure of 2.66 Kpa thereby recovering phenol.

Example 2

1.0 g of 48% aqueous solution of sodium hydroxide was used and the mixture was heated at a temperature of 180° C., and otherwise in the same manner as in Example 1, the primary crystallization filtrate was heat-treated.

Example 3

1.0 g of 48% aqueous solution of sodium hydroxide was used and the mixture was heated at a temperature of 200° C. and otherwise in the same manner as in Example 1, the primary crystallization filtrate was heat-treated.

Example 4

0.1 g of 48% aqueous solution of sodium hydroxide was used and the mixture was heated at a temperature of 200° C. and otherwise in the same manner as in Example 1, the primary crystallization filtrate was heat-treated.

Comparative Example 1

48% aqueous solution of sodium hydroxide was not added to the primary filtrate, and otherwise in the same manner as in Example 1, the primary crystallization filtrate was heat-treated.

The amount of the residue (bottom) generated by heat treatment of the primary crystallization filtrate in Examples 1 to 4 and Comparative Example 1 are shown in Table 1 together with the viscosities at 80° C. and the compositions of the residue.

In Table 1, the reduction rate of residue R(%) is defined by $R=((W_0-W)/W_0)\times 100$ wherein $W_0$ represents the amount of residue generated when the primary crystallization filtrate was heat-treated in the absence of an alkali catalyst (Comparative Example 1), and W represents the amount of the amount of residue generated when the primary crystallization filtrate was; heat-treated in the presence of an alkali catalyst (Examples 1 to 4).

TABLE 1

|  | Examples | | | | Comparative Examples |
|---|---|---|---|---|---|
|  | 1 | 2 | 3 | 4 | 1 |
| Residue (g) | 116.7 | 103.7 | 99.5 | 112.1 | 131.0 |
| Composition of Residue (g) | | | | | |
| Phenol | 3.3 | 0.5 | 0.0 | 0.9 | 0.8 |
| BPTMC | 13.6 | 3.3 | 2.6 | 21.8 | 47.6 |
| Others* | 99.8 | 99.9 | 96.9 | 89.4 | 82.6 |
| Rate of Reduction of Rsidue (%) | 10.9 | 20.8 | 24.0 | 14.4 | — |
| Viscosity of Residue at 80° C. (cps) | 1000 | 1000 | 1000 | a) | b) |

Notes:
*Decomposition products, etc.
a) Low viscosity liquid
b) Solid (viscosity unmeasurable)

What is claimed is:

1. A process for production of 1,1-bis(4-hydroxyphenyl)-3,3,5-trimethylcyclohexane which comprises reacting phenol with 3,3,5-trimethylcyclohexanone in the presence of an acid catalyst, adding an aqueous solution of an alkali to the resulting reaction mixture to neutralize it, removing a water phase from the thus neutralized reaction mixture, cooling the resulting oil phase to crystallize phenol adduct crystals of 1,1-bis(4-hydroxyphenyl)-3,3,5-trimethylcyclohexane while obtaining a primary crystallization filtrate, wherein the primary crystallization filtrate is heated to a temperature of 150–250° C. in the presence of an alkali catalyst in an inert gas atmosphere under a reduced pressure to thermally decompose 1,1-bis(4-hydroxyphenyl)-3,3,5-trimethylcyclohexane contained in the primary crystallization filtrate.

* * * * *